United States Patent [19]

Sagawa et al.

[11] Patent Number: 5,065,800
[45] Date of Patent: Nov. 19, 1991

[54] LIQUID CHARGING METHOD AND A LIQUID CHARGING APPARATUS

[75] Inventors: Takayoshi Sagawa; Shichisei Tani, both of Yokohama, Japan

[73] Assignee: Japan Tobacco Inc., Tokyo, Japan

[21] Appl. No.: 554,780

[22] Filed: Jul. 20, 1990

[30] Foreign Application Priority Data

Jul. 24, 1989 [JP] Japan .................. 1-188732

[51] Int. Cl.⁵ .................. B65B 3/30
[52] U.S. Cl. .................. 141/67; 141/238; 141/242
[58] Field of Search .............. 141/236, 237, 238, 240, 141/242, 244, 245, 246, 67

[56] References Cited

U.S. PATENT DOCUMENTS

| | | | |
|---|---|---|---|
| 2,749,005 | 6/1956 | Plusquellic | 141/242 X |
| 3,035,417 | 5/1962 | Hoyer | 141/244 X |
| 3,650,306 | 3/1972 | Lancaster | 141/238 |
| 4,461,328 | 7/1984 | Kenney | 141/67 |
| 4,511,534 | 4/1985 | Bennett, Jr. et al. | 141/245 X |
| 4,537,231 | 8/1985 | Hasskamp | 141/238 |

Primary Examiner—Ernest G. Cusick
Attorney, Agent, or Firm—Armstrong, Nikaido, Marmelstein, Kubovcik & Murray

[57] ABSTRACT

A method and apparatus for charging liquid into open, empty containers or capsules in a process of making liquid-filled capsules that are to be loaded into cigarette filters and may contain water, perfume or other substances to improve taste of cigarettes. Liquid is supplied to a hermetically enclosed space formed above a pit block and around the outer circumference thereof and then discharged from it to fill the liquid in a plurality of pits that pass through the pit block. Each pit has a narrow nozzle. A plurality of containers mounted on a tray are carried to a predetermined position under the pit block so that the containers are located immediately below the corresponding nozzles. An air pressure is supplied to the enclosed space to pressurize the liquid contained in the pits and thereby force the liquid to flow down the nozzles into the containers on the tray, which is then moved from under the pit block.

6 Claims, 3 Drawing Sheets

LIQUID CHARGING METHOD AND A LIQUID CHARGING APPARATUS

BACKGROUND OF THE INVENTION

The present invention relates to a variable-capacity liquid charging method and apparatus and more specifically to a method and an apparatus for charging a specified amount of liquid into open containers, which are empty capsules before being sealed with liquid in the process of making liquid-filled capsules.

In recent years, an ever-increasing variety of tobacco products are coming into market and, in the field of cigarette filters also, various kinds of filter products are being proposed.

For example, there is a cigarette filter loaded with a small capsule which, during smoking, is broken by pressure to let liquid in the capsule seep into the filter.

In such a filter, the liquid in the capsule may include water, perfume or other substances to improve taste and smell of the tobacco. By changing the liquid contents, it is possible to provide cigarettes with a variety of tastes meeting a growing diversity of consumers' needs.

A common method of making such filters involves filling the liquid into a container or capsule with one end open and hermetically sealing the opening with a lid.

A conventional technique for charging the liquid into the container consists in: installing the container with its opening facing up in a bottomed recess formed in the upper surface of a tray; positioning the tray at a specified location; and loading into the container a specified amount of liquid by a plunger pump which is located above the tray and can change its stroke to adjust the amount of liquid to be charged.

Such a liquid charging facility, however, has a very low efficiency as only one container is charged with liquid during each stroke of the pump. Therefore, to fill a large number of containers at a time requires arranging many pumps in parallel, which in turn increases not only the cost of the liquid charging equipment but also the design complexity, making the maintenance difficult.

SUMMARY OF THE INVENTION

This invention has been accomplished to solve the above-mentioned problems and to provide a method and an apparatus that make it possible to continuously charge a certain amount of liquid into small containers with very high efficiency by using a simple facility.

To achieve the above objective, a liquid charging method according to this invention comprises the steps of: supplying liquid into and then discharging it from an enclosed space formed above a pit block and around the outer circumference thereof so as to fill the liquid in a plurality of recesses or pits formed in the upper surface of the pit block, each of said pits opening at the upper surface of the pit block, said pits each having a specified liquid accommodating volume and also a small-diameter nozzle formed at the bottom thereof that pierces through the pit block; feeding a tray, on which an array of containers with their upper ends opened are installed; stopping and positioning said tray below the pit block at a specified liquid-charging position; closing the valve on the exhaust piping to hermetically isolate the enclosed space; supplying pressurized air into the enclosed space to apply pressure on the liquid in the pits and thereby force the liquid in the pits to flow down the small-diameter nozzles into the containers on the tray; and carrying the tray from below the pit block.

A liquid charging apparatus that realizes the above method comprises: a tray having an array of container accommodating recesses arranged at specified pitches for accommodating containers with their upper ends opened; a stop device for stopping said tray carried on a conveyor at a liquid-charging position; a pit block having an array of pits and small-diameter nozzles, both formed therein and arranged above the corresponding container accommodating recesses in the tray located at the liquid-charging position, said pits opening at the upper surface of the pit block, said small-diameter nozzles each extending downwardly from the bottom of each pit and opening at the underside of the pit block; a frame enclosing the outer circumference of the pit block to form a liquid accommodating portion between the frame and the pit block; liquid guide grooves formed in the upper surface of the pit block for communicating each of the pits with the liquid accommodating portion; a cover mounted on the upper edge of the frame to form a hermetically enclosed space inside the frame; a pressurized air piping for communicating the enclosed space with a pressurized air source through a valve; an exhaust piping for communicating the enclosed space with the open air through a valve; a liquid supply piping for communicating the liquid accommodating portion with a liquid tank through a supply pump; and a liquid discharge piping for communicating the liquid accommodating portion with the liquid tank; whereby a pressure is applied to the liquid in the pits to force the liquid to be charged into the containers on the tray at the liquid-charging position.

In order to prevent the liquid in the pits from falling down from the nozzles, the enclosed space formed above the pit block and around the outer circumference thereof is preferably depressurized by a vacuum source through a piping connecting the space with the vacuum source.

To adjust the amount of liquid accommodated in each pit, needles are provided in the cover in such a way that their positions can be adjusted and their front ends protrude into the pits.

The liquid guiding grooves may consist of a plurality of parallelly arranged communication grooves and a plurality of parallelly arranged through-grooves intersecting the communicating grooves, these two kinds of grooves being formed in the upper surface of the pit block. On the surface of the pit block where the array of pits are arranged in rows and columns, the communication grooves run between columns of pits and communicate at the ends with the liquid accommodating portion. The through-grooves are made to cross the communicating grooves, run directly through the rows of pits, and have their bottoms set higher than those of the communication grooves. The liquid guiding grooves may also be formed as either rows or columns of grooves which run between the adjacent rows or columns of the pits in such a manner as to cut a part of the upper portion of each pit.

With the above liquid charging method and apparatus, the liquid is charged into containers as follows.

The enclosed space is formed above the pit block and around its outer circumference, and defined by the cover and the frame. First, the supply pump is started to supply the liquid from the liquid tank through the liquid supply piping to the space. This causes the liquid to be delivered into the space until the liquid level rises to a certain level, higher than the top open ends of the pits.

Then, the liquid in the space is discharged through the liquid discharge piping. As a result, the pits, each of which has a specified amount of volume, are filled with the liquid.

The pits each have a nozzle which extends downwardly through the pit block and opens at the underside thereof. Since the nozzle diameter is very small, the liquid does not flow and get discharged from the nozzles. As mentioned above, depressurizing the space before supplying liquid into the space prevents with more certainty the liquid from flowing down.

When the tray carried on the conveyor is stopped at a specified position, the array of containers on the tray are positioned immediately below the corresponding nozzles.

When the valve on the exhaust piping is closed, the liquid accommodating portion is hermetically isolated. As the air pressure is supplied to the enclosed space through the pressurized air piping, the liquid in the pits are pressurized to flow down the narrow nozzles out into the containers below, filling each of the containers with a specified amount of liquid. The tray is then moved out of the liquid-charging position, thus completing one cycle of liquid charging process.

BRIEF DESCRIPTION OF THE DRAWINGS

FIGS. 1 through 4 illustrate embodiments of the invention; of which

FIG. 1 is an elevational cross section of a liquid charging apparatus according to the invention;

FIG. 2 is a plan view of a pit block;

FIG. 3 is a partial plan view of other embodiment of the pit block; and

FIG. 4 is a partial, elevational side view as seen from arrow X of FIG. 3.

DESCRIPTION OF THE PREFERRED EMBODIMENTS

Figure 1:
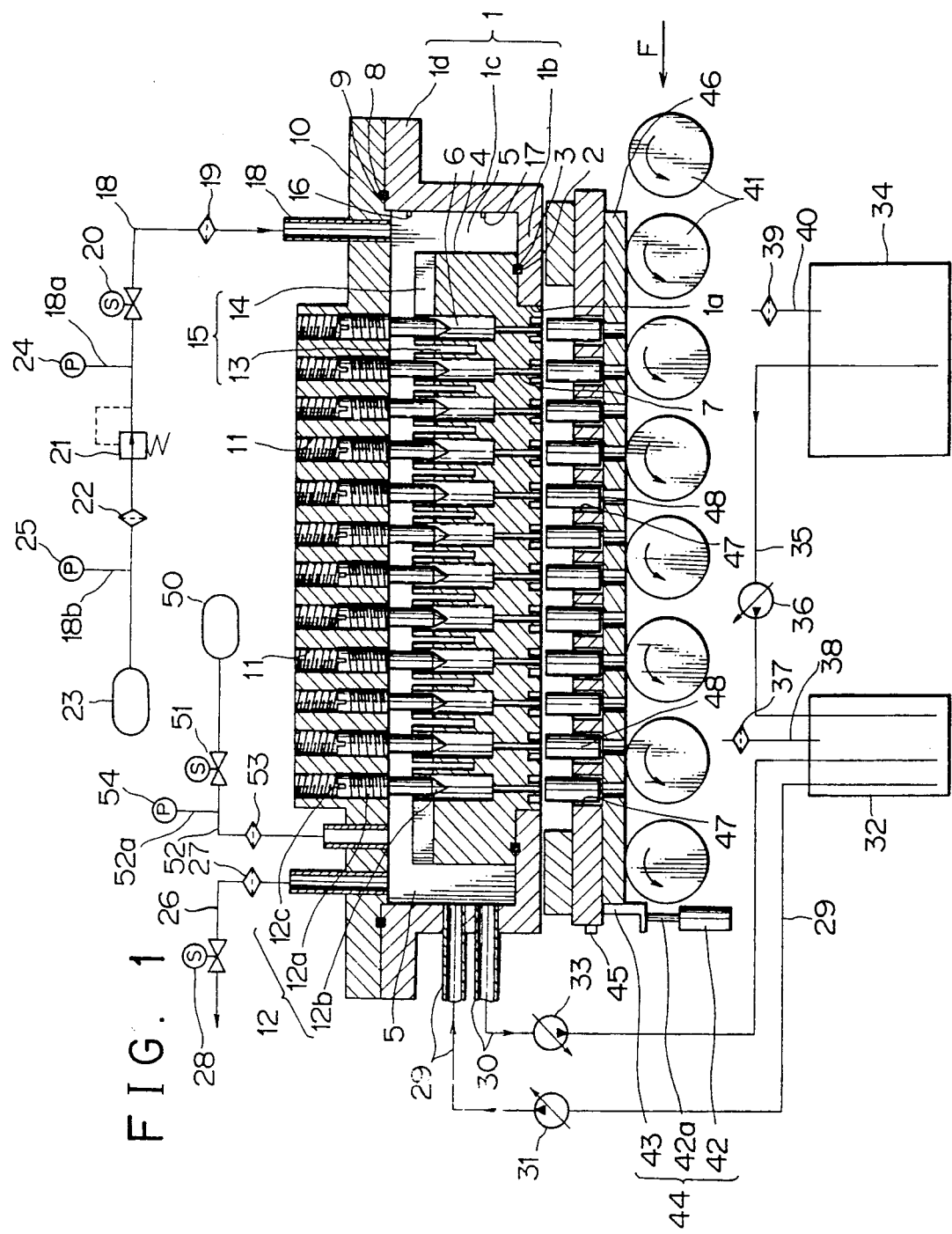

Preferred embodiments of the invention will be described by referring to the accompanying drawings. In FIG. 1 showing the vertical cross section of the liquid charging apparatus, a frame 1 consists of a bottom wall 1b with an opening 1a formed at the center, a side wall 1c rising from the periphery of the bottom wall 1b, and a flange portion 1d bent and extending radially outward from the upper edge of the side wall 1c.

The bottom wall 1b is provided with a seal groove 2 running parallel with the opening 1a. The seal groove 2 is fitted with a sealing material 3 such as O-ring to make water-tight the contact portion between the bottom wall 1b and a pit block 4 assembled onto the bottom wall 1b. On the outer circumference of the pit block 4 there is formed a liquid accommodating portion 5 which is enclosed by the bottom wall 1b and the side wall 1c.

Figure 2:
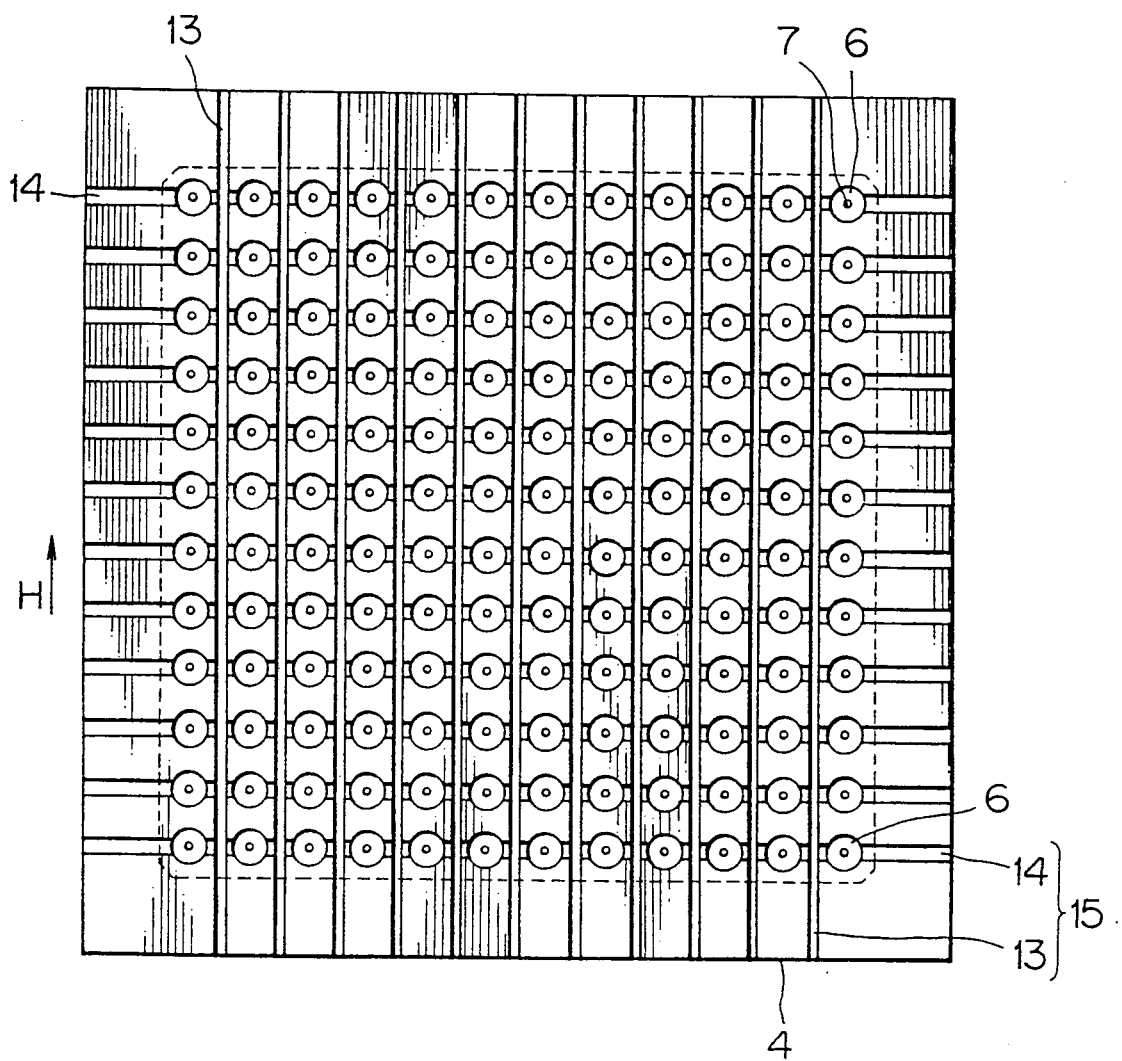

The pit block 4 has an array of upwardly opening circular pits 6 formed therein, which are equidistantly arranged in two orthogonal directions, twelve pits along a longitudinal side (in the widthwise direction in FIG. 1 and 2) and twelve pits along a lateral side (in the direction of arrow H in FIG. 2.

At the bottom of each pit 6 is formed a narrow nozzle 7 that passes through the pit block 4 and opens at the underside thereof. Since the diameter of the nozzles 7 is very small, liquid such as water filling the pits 6 is prevented from flowing out the nozzles 7 by the surface tension of the liquid. A groove is formed around the lower end of each nozzle 7.

On the upper side of the flange portion 1d of the frame 1 is formed a circular seal groove 8, into which a sealing material 9 is installed to keep air-tight the contact part between the frame 1 and a cover 10 mounted on the frame 1. Thus, a hermetically enclosed space is formed inside the frame 1.

The cover 10 is formed with threaded holes 11 at positions aligned with those of the corresponding pits 6. Into each threaded hole 11 is screwed a needle 12 that has a male thread 12a cut on its outer circumferential surface.

The needle 12 has a conically pointed front end 12b and at the rear end is engraved with a tool accommodating groove 12c to allow fine adjustment of the position of the front end 12b of the needle 12 protruding into the pit 6 by turning a tool like screwdriver engaged in the groove 12c.

While in this embodiment the screw is used in finely adjusting the position of the needle 12, it is also possible to use a friction mechanism.

On the upper side of the pit block 4 there are formed two groups of grooves perpendicularly crossing each other. One group is communication grooves 13 that run between the columns of pits 6 to reach the both ends of the pit block 4. The other group is through-grooves 14 that intersect the communication grooves 13 at right angles and extend directly through the rows of pits 6 to reach the both ends of the pit block 4. The communication grooves 13 and the through-grooves 14 constitute liquid guide grooves 15 that keep each pit 6 in communication with the liquid accommodating portion 5. (See FIG. 2.)

The bottoms of the through-grooves 14 are shallower than those of the communicating grooves 13 (see FIG. 1), so that as the liquid level in the liquid accommodating portion 5 rises, the liquid enters the communication grooves 13 first and then the through-grooves 14, from which it flows into the pits 6.

The side wall 1c, which constitutes the inner wall of the liquid accommodating portion 5, is provided with an upper limit detector 16 to detect the upper limit of the liquid level and with a lower limit detector 17 for the lower limit of the liquid level. The cover 10 receives a pressurized air piping 18 that opens into the liquid accommodating portion 5.

The pressurized air piping 18 communicates with a pressurized air source 23 through a filter 19, a valve 20, a pressure regulating valve 21 and a filter 22.

The valve 20 in this embodiment is a solenoid valve, but may be of a type that is operated manually or by air pressure to open or close the pressurized air piping. While in this embodiment a pressure tank is used as the pressurized air source 23, a compressor may be used instead.

The pressurized air piping 18 has branches 18a and 18b, to each of which is attached a pressure gauge 24, 25.

The cover 10 is also provided with a vacuum piping 52 that opens into the liquid accommodating portion 5. Vacuum piping 52 has a branch 52a which is attached to a pressure gauge 54. The vacuum piping 52 is connected to a vacuum source 50 via a filter 53 and a valve 51. The vacuum source 50 in this embodiment is a vacuum tank but may use a vacuum pump instead. This embodiment employs a solenoid valve for the valve 51, whereas a manually or pneumatically operated valve can also be used in opening or closing the vacuum piping.

The cover 10 is also fitted with an exhaust piping 26 which opens into the liquid accommodating portion 5 and communicates through a filter 27 with a valve 28 that opens into the external atmosphere. The valve 28 is a solenoid valve in this embodiment but may be other type of valve, as in the case of the valve 20.

The side wall 1c is provided with a liquid supply piping 29 opening into the liquid accommodating portion 5; it also receives a liquid discharge piping 30 opening into the liquid accommodating portion 5 at a position below the lower limit detector 17. The liquid supply piping 29 communicates with a liquid tank 32 through a supply pump 31. The liquid discharge piping 30 also communicates with the liquid tank 32 through a discharge pump 33.

The liquid in the tank 32 is replenished by a delivery pump 36 on a liquid delivery piping 35 that connects a large liquid reservoir 34 and the liquid tank 32.

The liquid tank 32 is provided at the top with a pipe 38 that communicates through a filter 37 with the open air; the liquid reservoir 34 is provided at the top with a pipe 40 that opens through a filter 39 into the open air. These pipes ensures that the interiors of the liquid tank 32 and the liquid reservoir 34 are kept at the atmospheric pressure.

Installed below the pit block 4 is a conveyor 41 of roller type, below which is further installed a stop device 44 which consists of a cylinder 42, a cylinder rod 42a, and a stopper 43 fixed at the end of the rod 42a. As the rod 42a is raised, the stopper 43 projects above the conveyor 41 to stop a material being carried at a specified position. The cylinder may be replaced with a solenoid for raising or lowering the stopper 43.

Immediately above the conveyor 41 is provided a detector 45, which detects a tray 46 being carried on the conveyor 41 in the direction of arrow F, at which time the stopper 43 is projected from the upper surface of the conveyor 41 stopping the tray 46 at a predetermined position below the pit block 4.

The widthwise position of the tray 46 (in a direction normal to the plane of the sheet of FIG. 1) is determined by guides (not shown) mounted on both sides of the conveyor. The tray 46 has a plurality of recessed portions 47 arranged in the same pitch and pattern as those of the pits 6. The recessed portions each accommodate a container or capsule 48 with the upper end opened. When the tray 46 is stopped and positioned at a specified location, the containers 48 are positioned immediately below the corresponding nozzles 7.

Now, the process of charging liquid into the containers by using the liquid charging apparatus with the above-mentioned construction will be explained.

Preparation

With the discharge pump 33 stopped, the valves 20 and 28 closed, and the valve 51 open, the supply pump 31 is started. This causes the liquid in the liquid tank 32 to flow through the liquid supply piping 29 into the liquid accommodating portion 5. And the liquid accommodating portion 5 is depressurized.

When the liquid level in the liquid accommodating portion 5 becomes higher than the communication grooves 13, the liquid flows into the communication grooves 13. Then as the liquid level moves further up and becomes higher than the through-grooves 14, the liquid enters from the communication grooves 13 into the through-grooves 14 and then into each of the pits 6 through two side openings at the upper part of each pit that communicate with the through-grooves 14. As the liquid pours into the pits 6, the air in the pits 6 is smoothly expelled through other than the side openings.

In this way, the residual air is not hindered from escaping by the liquid flowing into the pits 6 and therefore it is not trapped in the pits 6 as bubbles. In other words, even when the liquid inflow is fast, the specified amount of liquid can reliably be poured into the pits 6 at all times.

The liquid supplied into the pits 6 does not fall from the nozzles 7 because of the small diameter of the nozzle 7 and the surface tension of liquid and because the liquid accommodating portion 5 is depressurized.

When the level in the liquid accommodating portion 5 rises to the upper limit detector 16, the detector outputs a liquid detection signal to stop the supply pump 31 and start the discharge pump 33, followed by the valve 28 being opened and the valve 51 being closed to bring the liquid accommodating portion 5 into communication with the open air. The liquid is then returned to the liquid tank 32 through the liquid discharge piping 30.

When the liquid level goes down below the through-grooves 14, the liquid in the pits 6 is at the same level as the bottom of the through-grooves 14, retaining a specified amount of liquid in each pit 6. Under this condition, the liquid in the pits is stationary and its level low, so that it does not fall by gravity from the nozzles 7. In the case of water, for example, if the nozzle diameter is 0.5 mm, the water will not flow down the nozzle by gravity until the water column in the pit 6 is more than 30 mm high.

The amount of liquid received in the pit 6 can be finely adjusted with ease by engaging the tip of a screwdriver in the tool accommodating groove 12c of the needle 12 and turning it in either direction.

When the lower limit detector 17 detects the lowering liquid level in the liquid accommodating portion 5, the discharge pump 33 is stopped and the valve 28 closed. With the above steps taken, the preparation stage is now complete, Charging Liquid When the tray 46 being carried on the conveyor 41 in the direction of arrow F comes under the pit block 4, the detector 45 senses the approaching front end of the tray 46, causing the stopper 43 of the stop device 44 to move up.

As the front end of the tray 46 contacts the stopper 43, the containers 48 installed in the recessed portions 47 of the tray 46 are positioned immediately below the corresponding nozzles 7. At the same time the valve 20 is opened to supply the pressurized air from the pressurized air source 23 through the piping 18 into the hermetically enclosed space or the liquid accommodating portion 5. The air pressure supplied causes a predetermined amount of liquid in each of the pits 6 to fall out of the nozzles 7 into the corresponding containers 48 below. The groove formed around the bottom outlet of the nozzle prevents the liquid, when it drops, from spreading over the underside of the pit block 4 and falling onto undesired parts of the tray. This ensures that the precise amount of liquid can reliably be supplied into each of the containers 48.

With the containers filled with the liquid, the stopper 43 of the stop device 44 is lowered and the tray 46 is again moved in the direction of arrow F on the conveyor 41 to the next process, where the openings in the containers are sealed to form the liquid-filled capsules.

After a specified period of time, the valve 20 is closed to stop a further supply of pressure and the valve 51 is opened to depressurize the hermetically enclosed space. At the same time the supply pump 31 is started to load liquid into the pits 6 in a way similar to that in which the above-mentioned preparation process was carried out.

Now, one cycle of liquid charging process is complete and this process is repeated in the same manner, continuously charging the predetermined amounts of liquid into a large number of containers with high efficiency.

This kind of liquid charging in small containers can be applied not only to tobaccos but also to liquid seasonings, perfumes, and drugs.

Figure 3:
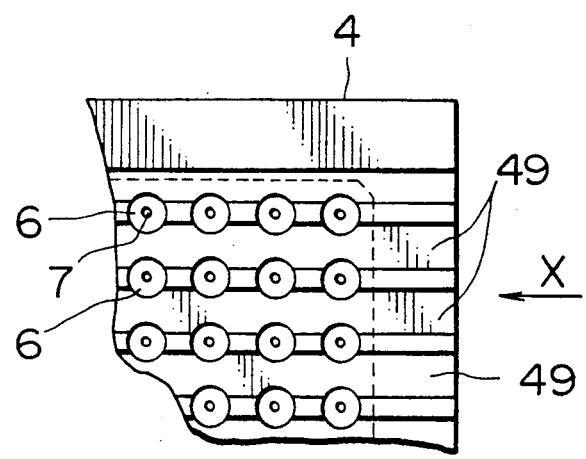
Figure 4:
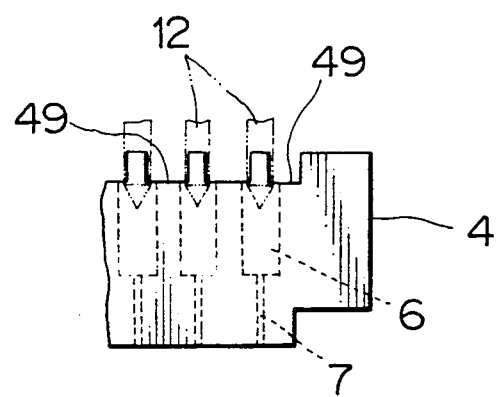

FIGS. 3 and 4 show another embodiment of the liquid guide grooves 15 formed in the surface of the pit block 4. FIG. 3 is a plan view of the essential portion of the pit block and FIG. 4 is a partial cross section of the same as seen from arrow X in FIG. 3. In this embodiment, liquid guide grooves 49 are provided between the rows of pits 6 in such a way that they cut a part of the upper circumferential portion of the pits 6.

The bottom of the liquid guide grooves 49 is equal in height to the bottom of the through-grooves 14 of the first embodiment. The liquid flowing from the guide grooves 49 into the pits 6 enters through the upper two cut openings of each pit, so that the air in the pits can safely escape from other than the cut openings as in the first embodiment, without any residual air being trapped in the pits as bubbles.

Advantages of the Invention

The advantages of the invention may be summarized as follows.

(1) In the liquid charging method and apparatus of this invention, narrow nozzles, which do not let liquid fall through under the atmospheric pressure, are provided to the bottom of the pits, each of which has a specified liquid receiving capacity. By applying pressure to the liquid in the pits, it is possible to deliver a certain amount of liquid into a plurality of containers arranged below at once. Thus, liquid charging into a plurality of containers can be done efficiently in a very short time.

The application of the liquid charging method and apparatus of the invention is not limited to the field of tobacco. It can also be applied to other technical fields involving the process of charging liquid into small containers. For example, it may be utilized in the process of charging liquid seasonings, perfumes and drugs into small capsules.

(2) Since the pits are replenished with liquid after the liquid was driven out of the pits through the nozzles, the liquid charging into the containers can be performed repetitively and continuously.

(3) Since the needles with their front ends inserted into the corresponding pits can easily be adjusted in position, it is very easy to finely adjust the amount of liquid loaded in each pit.

(4) In place of a plunger pump which is complex in construction, pits each attached with a nozzle at the bottom are used. This construction is simple and has high durability, reducing the probability of failure and making inspection and maintenance easier. This construction also makes the cost of manufacture lower than that of the conventional liquid charging apparatuses.

(5) Since the liquid guide grooves are formed so as to cut a part of the upper portion of each pit, the liquid flowing into the pit does not hinder the air from escaping from the pit, so that there is no possibility of any residual air bubbles being formed which would reduce the amount of liquid supplied to the pit.

What is claimed is:

1. A liquid charging apparatus comprising:

a conveyor;

a tray disposed on the conveyor, the tray having an array of container-accommodating recesses arranged at specified pitches for accommodating containers with their upper ends opened;

a stop device for stopping said tray on the conveyor at a liquid-charging position;

a pit block having an array of pits and small-diameter nozzles, both formed therein and arranged above the corresponding container-accommodating recesses in the tray located at the liquid-charging position, said pits opening at an upper surface of the pit block, said small-diameter nozzles each extending downwardly from a bottom of each pit and opening at an underside of the pit block;

a frame enclosing an outer circumference of the pit block to form a liquid-accommodating portion between the frame and the pit block;

liquid guide grooves formed in an upper surface of the pit block for communicating each of the pits with the liquid-accommodating portion;

a cover mounted on an upper edge of the frame to form an enclosed space inside the frame;

an exhaust piping for communicating the enclosed space with the open air through a valve;

a pressurized air piping for communicating the enclosed space with a pressurized air source through a valve, whereby a pressure is applied to the liquid in the pits to force the liquid to be charged into the containers on the tray at the liquid-charging position;

a liquid supply piping for communicating the liquid-accommodating portion with a liquid tank through a supply pump; and a liquid discharge piping for communicating the liquid-accommodating portion with the liquid tank.

2. A liquid charging apparatus as claimed in claim 1, wherein the pits are arranged in rows and columns, and said liquid guide grooves formed in the upper surface of the pit block consist of: a plurality of parallelly arranged communication grooves, running between the columns of the pits and communicating at their ends with the liquid-accommodating portion; and a plurality of parallelly arranged through-grooves which cross the communication grooves, pass directly through the rows of pits, and have their bottoms set higher than those of the communication grooves.

3. A liquid charging apparatus as claimed in claim 1, wherein said liquid guide grooves are formed in the upper surface of the pit block in such a manner that they run between the parallelly arranged rows of pits and cut a part of the upper portion of each pit and that their ends communicate with the liquid accommodating portion.

4. A liquid charging apparatus as claimed in claim 1, wherein the valve is a first valve, further comprising a vacuum piping for communicating said enclosed space in the frame with a vacuum source through a second valve.

5. A liquid charging apparatus as claimed in claim 3, wherein a circular groove is formed around the bottom outlet of each of the small-diameter nozzle provided in the pit block.

6. A liquid charging apparatus as claimed in claim 1, wherein the enclosed space formed by the pit block, the frame and the cover is hermetical, further comprising a plurality of position-adjustable needles are provided in the cover, one needle being provided for each pit, one end of each needle projecting into each pit.

* * * * *